US00PP29632P2

(12) United States Plant Patent
Egger

(10) Patent No.: US PP29,632 P2
(45) Date of Patent: Aug. 28, 2018

(54) ***HEUCHERA* PLANT NAMES 'TNHEUNES'**

(50) Latin Name: ***Heuchera* hybrid**
Varietal Denomination: TNHEUNES

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/731,558

(22) Filed: Jun. 27, 2017

(51) Int. Cl.
*A01H 5/02* (2018.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by purple to silver colored leaves with dark to green veins, medium large, slightly lobed, geranium-like leaves, light pink flowers in spring on upright flowering stems in spring on upright flowering stems, good sun tolerance, a large, mounding habit with excellent crown count, and excellent vigor.

1 Drawing Sheet

Botanical denomination: *Heuchera* hybrid.
Variety designation: 'TNHEUNES'.

BACKGROUND OF THE INVENTION

The present invention relates to a new and distinct cultivar of *Heuchera* and given the cultivar name of 'TNHEUNES'. *Heuchera* is in the family Saxifragaceae. *Heuchera* 'TNHEUNES' originated as a controlled cross using *Heuchera* 'K967-3', a proprietary, unpatented, unnamed plant as the seed parent, and *Heuchera* 'K973-4', a proprietary, unpatented, unnamed plant as the pollen parent. These parents are a result of breeding using hardy *Heuchera richardsonii* with proprietary hybrid lines. *Heuchera* 'TNHEUNES' was bred to be a hardy, large, landscape plant.

Compared to the seed parent, *Heuchera* 'K967-3', the new cultivar has a larger habit.

Compared to the pollen parent, *Heuchera* 'K973-4', the new cultivar has a larger habit and larger brighter silver leaves.

Compared to *Heuchera* 'Silver Light', U.S. Plant Pat. No. 15,067, the new cultivar has larger, rounder leaves with less prominent lobing and a bigger habit.

Compared to *Heuchera* 'Silver Scrolls', U.S. Plant Pat. No. 12,066, the new cultivar has a larger habit and leaves and more upright inflorescences.

Compared to *Heuchera* 'Saturn', an unpatented plant, the new cultivar has a larger habit and leaves.

This new *Heuchera* is uniquely distinguished by:

1. purple to silver colored leaves with dark to green veins,
2. medium large, slightly lobed, geranium-like leaves,
3. light pink flowers in spring on upright flowering stems,
4. good cold and sun tolerance,
5. a large, mounding habit with excellent crown count, and
6. excellent vigor.

This new cultivar has been reproduced only by asexual propagation (tip cuttings and tissue culture using growing tips). Each of the progeny exhibits identical characteristics to the original plant. Asexual propagation in 2013 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a three-year-old plant of *Heuchera* 'TNHEUNES' growing in the trial bed in partial shade in July in Canby, Oreg.

FIG. 2 shows two-year-old plants the new cultivar in late June in the trial beds in part shade in Canby, Oreg.

DETAILED PLANT DESCRIPTION

The following is a detailed description of the new *Heuchera* cultivar based on observations taken in July of two-year-old specimens growing in the trial field in part shade in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5$^{th}$ edition, 2007.

Plant:

*Form.*—Basal rosette, herbaceous perennial.
*Hardiness.*—USDA Zone 4 to 9.
*Size.*—32 cm tall from top of the foliage to the ground and 53 cm wide.
*Number of crowns.*—About 17.
*Habit.*—Medium large, mounding.
*Vigor.*—Excellent.

Leaf:

*Type*.—Simple.

*Arrangement*.—Rosette.

*Shape*.—Broadly ovate to orbicular.

*Number*.—About 300.

*Blade size*.—Grows to 11 cm long and 11 cm wide.

*Venation*.—Palmate.

*Lobing/division*.—7 shallow palmate lobes.

*Margins*.—Crenate.

*Apex*.—Mucronulate.

*Base*.—Cordate, strongly overlapping.

*Surface texture*.—Glandular-puberulent on both sides.

*Leaf rugosity*.—Absent.

*Petiole description*.—Grows to 19 cm long and 4 mm wide, glandular hairs, Greyed Purple 187A.

*Leaf color*.—New leaves, topside Grey 101D tinted Purple N79B to N77C with veins Greyed Purple186A, bottom side Greyed Purple 187A; older leaves Grey 201C with veins Greyed Green N189B, bottom side Greyed Purple 187A.

Inflorescence:

*Size*.—Grows to 6.5 cm wide and 17 cm long.

*Type*.—Upright thyrse.

*Number of flowers per thyrse*.—About 90.

*Flower density*.—Moderate to light.

*Number of thyrse*.—About 20.

*Peduncle*.—Grows to 44 cm long and 3.5 mm wide at base, glandular hairs, Greyed Purple 187A.

*Pedicel*.—Grows to 5 mm long, with glandular hairs, Greyed Purple 187A.

*Bloom period*.—Late April to July in Canby, Oreg.

Flower bud:

*Size*.—3 mm wide and 5 mm long.

*Description*.—Glandular puberulent, ovoid, down facing.

*Color*.—Red Purple 61A on bottom ⅓ and 64A on top ⅔.

Flower:

*Type*.—Perfect.

*Shape*.—Campanulate.

*Attitude*.—Side and down-facing.

*Size*.—6 mm long and 3 mm wide.

*Corolla description*.—5 petals, each 1.5 mm long and 0.8 mm wide, spatulate, margins entire, tip acute, glandular-puberulent on back side, glabrous on the inside, Red Purple 69C on both sides.

*Calyx description*.—Campanulate, 6 mm long and 3 mm wide, with 5 lobes with wide sinuses divided ½ way to the base, each 2 mm wide and 3 mm long, oblong in shape, back side glandular-puberulent, glabrous inside, tip obtuse, margin entire, Red Purple 70D inside, Red Purple 63C blending to 64A at tips on outside.

*Stamen description*.—5 in number, filaments 3 mm long, White NN155A, anthers 0.7 mm long, Greyed Orange 172A, pollen Orange 25A.

*Pistil description*.—1, 2-beaked, 5 mm long and 2 mm wide, ovary 2 mm long and 2 mm wide, Green Yellow 1C, style 3 mm long, White N155A.

*Fragrance*.—None.

*Lastingness*.—Each thyrse blooms for about 3 weeks on the plant.

Fruit and seed: None seen.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

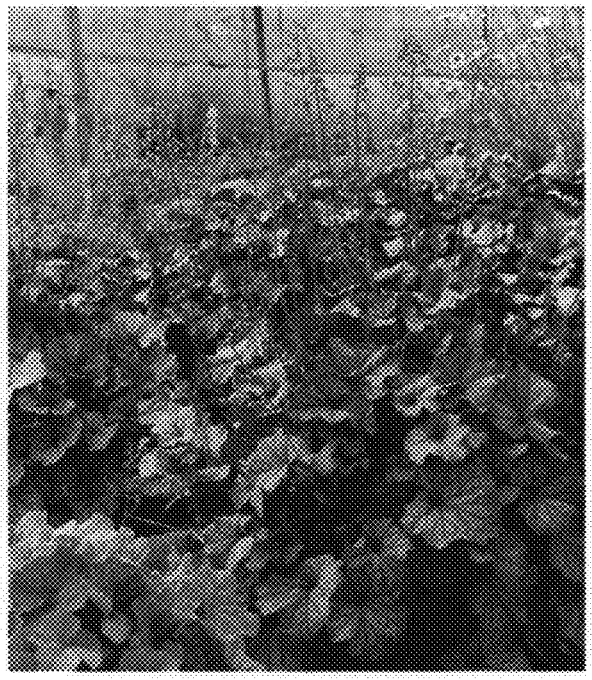

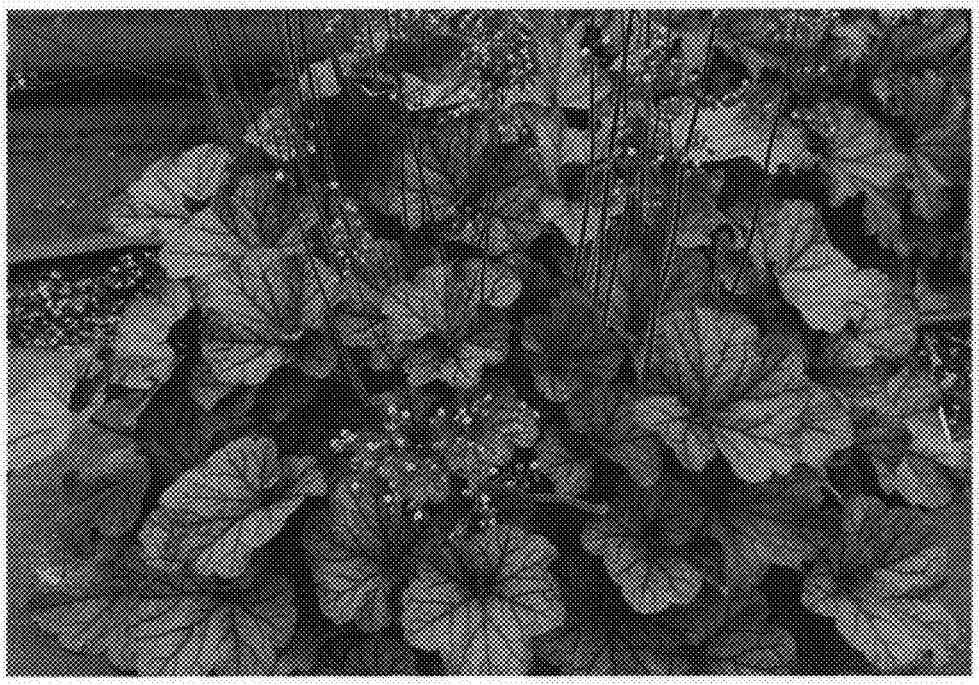
FIG. 1 above,
FIG. 2 below